United States Patent [19]

Venkataramu et al.

[11] 4,332,946

[45] Jun. 1, 1982

[54] RESOLUTION ENHANCING MALEIMIDE SPIN LABEL FOR BIOLOGICAL EPR STUDIES

[75] Inventors: Sindhaghatta D. Venkataramu; Donald E. Pearson; Albert H. Beth, all of Nashville, Tenn.

[73] Assignee: Vanderbilt University, Nashville, Tenn.

[21] Appl. No.: 250,137

[22] Filed: Apr. 3, 1981

[51] Int. Cl.$^3$ .......................................... C07D 401/04
[52] U.S. Cl. ................................................. 546/208
[58] Field of Search ........................................ 546/208

[56] References Cited

U.S. PATENT DOCUMENTS 3,481,952 12/1969 McConnell et al. ................ 546/208
3,534,048 10/1970 Murayama et al. ................. 546/208
3,775,401 11/1973 Pfirrmann ........................... 546/208

OTHER PUBLICATIONS

Beth et al., *Chem. Phys. Letts.*, vol. 69, pp. 24–28 (1980).

*Primary Examiner*—John M. Ford

[57] ABSTRACT

An improved maleimide spin label, namely, N-($^{15}$N-oxyl-2,2,6,6-tetra-methyl-4-piperidinyl-d$_{17}$) maleimide is provided for EPR spectroscopic investigations of biomedically relevant problems. Isotopic substitution of nitrogen-15 in the N—O bond and deuterium in the methyl groups (-CD$_3$) and in all positions of the piperidine ring results in simplification of the EPR spectrum, greatly improved resolution, and a marked increase in signal intensity.

1 Claim, No Drawings

RESOLUTION ENHANCING MALEIMIDE SPIN LABEL FOR BIOLOGICAL EPR STUDIES

GRANT REFERENCE

This invention was made in the course of research supported in part by BRSG Grant SO7-RR05424 and Grant GM-07884 awarded by the Biomedical Research Support Grant Program, Division of Research Resources, National Institutes of Health and in part by Muscular Dystrophy Association.

BACKGROUND AND PRIOR ART

U.S. Pat. No. 3,481,952 discloses a class of maleimide compounds which can be used as spin labels for biological molecules to study their motional characteristics by electron paramagnetic resonance (EPR) spectroscopy. With reference to such maleimide spin labels, the widely used compound has been N-(1-oxyl-2,2,6,6-tetramethyl-1-piperdinyl-oxyl)maleimide ($^{14}$N-HMSL). Beth, et al have shown that $^{14}$N-HMSL can be improved as a spin label with respect to its sensitivity and resolution capability by substitution of deuterium for all hydrogens in the heterocyclic ring containing the paramagnetic group. Beth, et al, *Chem. Phys. Letts.* (1980), 69, 24–28. The specific compound disclosed was N-(1-oxyl-2,2,6,6-tetramethyl-4-piperidinyl)maleimide ($^{14}$N-DMSL).

DISCLOSURE OF INVENTION

It has now been discovered that a remarkable improvement in EPR spectroscopic properties for biomedical applications can be realized by isotopic substitution of nitrogen-15 in the N—O bond of the spin label $^{14}$N-DMSL. In the $^{15}$N-compound, it is essential that deuterium has been substituted for the hydrogens in the CH$_3$ groups and in all positions of the piperidine ring. The resulting compound, which comprises the improved spin label of the present invention is N-($^{15}$N-oxyl-2,2,6,6-tetramethyl-4-piperidinyl-d$_{17}$)maleimide ($^{15}$N-DMSL), which is also represented by the following structural formula:

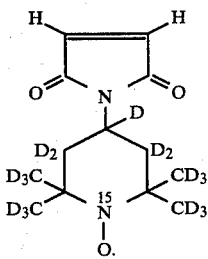

The novel spin label of this invention when employed in investigations of biological and biomedical problems results in simplification of the EPR spectrum, and an increase in signal intensity. More specifically, the spin label of this invention, $^{15}$N-DMSL, results in (1) a two line pattern in its EPR spectrum, (2) an approximately ten-fold increase in signal intensity relative to $^{14}$N-HMSL and (3) a decrease in line width. These features of the spin label $^{15}$N-DMSL permit highly resolved EPR spectra to be obtained with biological molecules (e.g. enzymes, red blood cell membranes, etc.). When such molecules are bound to the label $^{15}$N-DMSL, a noteworthy feature in the EPR spectra is the absence of any overlap of the two $^{15}$N nuclear manifolds. Such improved sensitivity and resolution can be expected to greatly enhance the value of the $^{15}$N-DMSL label for clinical tests and diagnostic procedures.

Comparable results cannot be achieved with the prior art compounds $^{14}$N-HMSL or $^{15}$N-DMSL, as identified above. With the spin label of this invention, $^{15}$N-DMSL, resolution is markedly improved with respect to all biological systems, and at least for some biomolecules complete resolution of the complex can be obtained, a result never before achieved with respect to EPR studies of biologically significant molecules with maleimide spin labels. For example, a comparison of glyceraldehyde-3-phosphate dehydrogenase (GAPDH) spin labelled with $^{15}$N-DMSL, $^{14}$N-DMSL, or $^{14}$N-HMSL shows clear separation of the two nuclear manifolds in the $^{15}$N-DMSL EPR spectrum, whereas the central region of the $^{14}$N-DMSL spectrum with three manifolds displays overlapping signals which are even more pronounced in the $^{14}$N-HMSL spectrum. Computer simulation of the spectra for $^{15}$N-DMSL is therefore facilitated and highly quantitative.

The spin label of this invention, $^{15}$N-DMSL, can be synthesized from available reagents. An example of a suitable synthesis procedure is set out below.

SYNTHESIS

Preparation of Spin Label Compound N-($^{15}$N-oxyl-2,2,6,6-tetramethyl-4-piperidinyl-d$_{17}$)maleimide (hereinafter $^{15}$N-DMSL) was accomplished as follows: To a mixture of acetone-d$_6$ (100 g, 1.56 mole) and 4–20 mesh size calcium chloride (37 g) in a 1 L three-necked flask fitted with a gas inlet, an efficient mechanical stirrer and a Y-joint carrying a 0°–50° C. thermometer and a dry ice condenser was introduced, over a period of 4 days, $^{15}$N-deuterated ammonia (15.75 g, 0.75 mole) in approximately six equal lots. The temperature of the reaction mixture was maintained at 30°–35° C. during the introduction of $^{15}$ND$_3$. After allowing the reaction mixture to remain at room temperature for 4 days, during which time it turned red and became thick, unreacted acetone-d$_6$ (17.6 g, 0.12 mole) was recovered by distillation, bp 35°/100 mm. To the resulting cake was added, with cooling, a solution of sodium deuteroxide (25 ml of 40% NaOD) dropwise with vigorous stirring. The liberated oil was thoroughly extracted with ether (5×200 ml) and the organic layer was dried (MgSO$_4$). After evaporation of the solvent, the residue was distilled in vacuum. The fraction, bp 80°–82° C./12 mm, which crystallized in the receiver (30.1 g) was collected to give $^{15}$N-2,2,6,6-tetramethylpiperidine-4-one-d$_{17}$ (Compound A). Recrystallization from CCl$_4$ afforded pure piperidone, Compound A, (26 g, 29%) which melted at 36–38°, (Lit. mp 35.5–36°, Rozantsev, *Free Nitroxyl Radicals*, p. 203, Plenum Press, N.Y., 1970; Sosnovsky and Konieczny, *Synthesis*, 735 (1976). $^1$H NMR (CCl$_4$) revealed a high degree of deuteration in all positions of piperidone.

Oxime deuterochloride of $^{15}$N-2,2,6,6-tetramethyl-4-piperidone-d$_{17}$ (hereinafter Compound B) was prepared as follows: To a solution of Compound A (11.20 g, 0.0647 mole) in 22 ml ethanol-d was added, with ice cooling and stirring, a solution of ND$_2$OD.DCL (10.0 g, 0.136 mole) and anhydrous sodium deuteroacetate (5.78 g, 0.068 mole) in 20 ml D$_2$O in a nitrogen atmosphere. An exothermic reaction ensued and a white solid separated. After allowing the reaction mixture to warm up to room temperature, it was gently heated on a steam bath for 5 hr., and allowed to stand overnight. The white crystalline deuterochloride that had separated was filtered, washed with 5 ml cold ethanol-d and dried in the desiccator to give 10.2 g oxime deuterochloride, Compound B, mp 285°–290° (dec); (Lit. mp about 300° with dec, Oickerman and Linderall, *J. Org. Chem.,* 14, 530 (1949)). The mother liquor was concentrated which on standing in the refrigerator overnight gave 2.2 g of slightly impure material mp 280°–285° C. (dec) and was combined with the first crop. After drying at 100° C./30 mm for 6 hr. in an oven, the total yield of the oxime deuterochloride, Compound B, was 12.1 g (82%) and was used in the subsequent step without further purification.

$^{15}$N-2,2,6,6-Tetramethyl-4-aminopiperidine-d$_{20}$, Compound C, was prepared as follows: The procedure of Misharin et al, *Izv. Akad. Nauk. SSSR. Ser. Khim Engl.* Ed. 23, 1822 (1974), was adopted, except that LiAlD$_4$ was used in place of LiAlH$_4$ and excess of the reducing agent was destroyed in a deuterated medium. To a stirred suspension of LiAlD$_4$ (5 g, 0.12 mole) in 250 ml anhydrous ether (distilled over LiAlH$_4$), the oxime deuterochloride, Compound B, (12.1 g, 0.053 mole) was added cautiously from a solid addition flask at such a rate there was continuous boiling of the solvent. The mixture was gently heated for 10 hr., and then cooled. Excess LiAlD$_4$ was cautiously destroyed (N$_2$) by successive addition of 5 ml D$_2$O, 5 ml NaOD in D$_2$O and 15 ml D$_2$O as described in Fieser and Fieser, *Reagents for Organic Synthesis,* Vol. I, p. 584, (Wiley & Sons, N.Y. 1967). The granular precipitate was filtered, pressed on the filter paper and washed with several portions of anhydrous ether. The organic extract was dried (anhydr. K$_2$CO$_3$) and the solvent removed under reduced pressure. Distillation of the residue in vacuum furnished 6.2 g (65%) of the amine as a colorless mobile liquid, Compound C, bp 58°–60°/2 mm; (Lit. 60°–62°/2 mm, Mischarin et al, cited above).

$^{15}$N-2,2,6,6-Tetramethyl-4-acetylaminopiperidine-d$_{22}$, Compound D, was prepared by the procedure of Rozantsev et al, *Free Nitroxyl Radicals,* p. 230 (Plenum Press, N.Y., 1970). Thus, acetic anhydride-d$_6$ (10 g, 0.092 mole) was added dropwise to a cooled (10° C.) and magnetically stirred solution of the amine, Compound C, (6.2 g, 0.035 mole) in 16 ml anhydrous ether. The temperature of the reaction mixture was not permitted to rise above 15°. After stirring for 30 minutes, the mixture was diluted with 25 ml D$_2$O to give a clear solution, cooled to 10° C. and alkalified with 10 ml of 5% NaOD. The solid was filtered and washed with D$_2$O to give 6.4 g of the pure acetate, Compound D, mp 120°–124° C.; Lit. mp 120°–122° C., Rosantsev, p. 230, cited above. The aqueous layer was extracted with ethyl acetate (3×50 ml), dried (anhydr. K$_2$CO$_3$) and the solvent was removed in vacuo to give an additional quantity of the acetate (1.0 g) Compound D. The total quantity of the acetate amounted to 7.4 g (95%) and was used in the next step without further purification.

$^{15}$N-2,2,6,6-Tetramethyl-4-amino-piperidine-1-oxyl-d$_{19}$, Compound E, was prepared by the procedure of Rozantsev et al, cited above, pp. 213, 231. To a solution of the acetate, Compound D, (7.4 g, 0.033 mole) in 15 ml methanol-d and 30 ml D$_2$O were added sodium tungstate (0.5 g), sodium salt of EDTA (0.5 g) and 9.5 ml of 30% H$_2$O$_2$ diluted with 30 ml D$_2$O. The reaction mixture was allowed to remain in the refrigerator overnight and then for 10 days at room temperature in the dark, at which time it acquired a red color. After saturating the reaction mixture with K$_2$CO$_3$, the solution was extracted with dry ether (5×100 ml) and the combined organic layer was dried (anhydr. K$_2$CO$_3$). Removal of the solvent on the rotary evaporator furnished an orange yellow solid (8.5 g). This was suspended in 25 ml of 15% NaOD and the contents stirred and boiled for 16 hrs. The cooled solution was suction filtered, saturated with K$_2$CO$_3$ and extracted with ether (5×100 ml). After being stirred with anhydrous MgSO$_4$, the solvent was rotoevaporated and the red oil (5.8 g) was distilled in vacuum using a short distillation head. The yield of the amino radical, Compound E, was 4.0 g (63%), bp 80–85%/2 mm; Lit. 97°–98°/4 mm; Rozantsev, cited above, p. 231. TLC (HCCl$_3$:MeOH, 9:1 showed a single spot (R$_f$=0.66) identical with an undeuterated sample.

$^{15}$N-(1-Oxyl-2,2,6,6-tetramethyl-4-piperidinyl) maleimide-d$_{17}$, the Spin Label, was prepared by the procedure of Berliner, *Spin Labelling: Theory and Applications,* p. 213, Academic Press, N.Y. (1976). The amino radical, Compound E, (1.0 g, 5.2 mmole) in 10 ml dry ether was added to maleic anhydride (0.5 g, 5.2 mmole) dissolved in 30 ml ether. After being stirred for 1 hr. the precipitated orange solid was filtered, washed with 10 ml of ether to provide maleamic acid, Compound F, (1.40 g, 93%); mp 170–172; Lit. mp 170°, Mischarin et al, *Isv. Akad. Nauk. SSR Sev. Khim Engl.,* Ed. 213:2434 (1974). The crude acid, Compound F, (1.40 g, 4.86 mmole), anhydrous sodium acetate-d$_3$ (0.2 g, 2.43 mmole) and 10 ml of acetic anhydride-d$_6$ were heated at 100° for 3 hrs. Excess acetic anhydride was removed under vacuum (bp 40°/1 mm) and the residue was dissolved in small amounts of hot benzene. The combined organic extract was passed through a short column of silica gel to remove inorganic material. Removal of solvent in a rotoevaporator afforded a thick red gum (1.4 g). TLC (HCCl$_3$) showed this to be a mixture of the desired Spin Label, and isomaleimide, Compound G. Separation of the desired maleimide from the isomer was achieved by column chromatography on silica gel (30 g, 60–200 mesh size) employing chloroform as eluent. The maleimide spin label was eluted first and had the R$_f$ value of 0.75. Fractions with this R$_f$ value were pooled together and recrystallized from cyclohexane several times to furnish chemically pure N-($^{15}$N-oxyl-2,2,6,6-tetramethyl-4-piperidinyl-d$_{17}$)maleimide, as an orange yellow solid (0.5 g, 38%). After drying at 80°/30 mm for 12 hours, the maleimide spin label compound melted at 107°–108°; Lit. Mischarin et al, cited above, p. 2434. The mother liquor was concentrated and rechromatographed on silica gel (10 g) and the maleimide spin label sublimed at 130°–140° C./50 millitor to give 0.3 g (23%) of slightly impure material, mp 106°–107° C.

In the foregoing example melting points were determined with a Thomas-Hoover capillary melting point apparatus and are uncorrected. Proton NMR spectra were obtained on a Joel MH-100 nuclear magnetic resonance spectrometer with TMS as an internal standard. Mass spectra (70 ev) were recorded on a LKB-9000 mass spectrometer by direct insertion. The deuterium composition was determined on the molecular ion. ESR spectra were recorded on a Varian E-109 spectrometer equipped with a TM$_{110}$ cavity. Thin layer chromatography (TLC) analyses were carried out on Eastman Chromagram 13181 precoated silica gel plates. Spots were revealed by exposure to UV light or iodine vapor. Reagents and solvents were purified when necessary.

Literature melting or boiling points (Lit.) refer to undeuterated compounds.
We claim:
1. As a resolution enhancing spin label for biomedical EPR applications, the compound
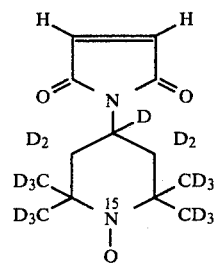
N-($^{15}$N-oxyl-2,2,6,6-tetramethyl-4-piperidinyl-d$_{17}$)maleimide.
* * * * *

UNITED STATES PATENT OFFICE
CERTIFICATE OF CORRECTION

Patent No. 4,332,946　　　　　　　　Dated June 1, 1982

Inventor(s) Sindhaghatta D. Venkataramu et al

It is certified that error appears in the above-identified patent and that said Letters Patent are hereby corrected as shown below:

Column 1, line 20 delete "-oxyl", so that the corrected name will read "-piperdinyl)maleimide"; and Col. 2, line 5 change "$^{15}N$" to "$^{14}N$".

Signed and Sealed this

Fifth Day of October 1982

[SEAL]

Attest:

GERALD J. MOSSINGHOFF

Attesting Officer　　　Commissioner of Patents and Trademarks